United States Patent [19]

Saari et al.

[11] Patent Number: 5,183,815
[45] Date of Patent: Feb. 2, 1993

[54] NOVEL BONE ACTING AGENTS

[75] Inventors: Walfred S. Saari, Lansdale; Gideon A. Rodan, Bryn Mawr; Thorsten E. Fisher; Paul S. Anderson, both of Lansdale, all of Pa.

[73] Assignee: Merck & Co., Inc., Rahway, N.J.

[21] Appl. No.: 839,741

[22] Filed: Feb. 19, 1992

Related U.S. Application Data

[63] Continuation of Ser. No. 644,178, Jan. 22, 1991, abandoned.

[51] Int. Cl.$^5$ ...................... A61K 31/56; A61K 31/58
[52] U.S. Cl. ..................................... 514/172; 514/174; 514/176; 514/178; 514/181; 514/182; 540/5; 552/506; 552/507
[58] Field of Search ............... 552/506, 507; 514/178, 514/181, 182, 172, 174, 176; 540/5

[56] References Cited

U.S. PATENT DOCUMENTS

| | | | |
|---|---|---|---|
| 3,664,975 | 5/1972 | Kerst | 260/2.5 |
| 3,957,858 | 5/1976 | Kerst | 260/502.4 |
| 3,962,318 | 6/1976 | Kerst | 260/502.4 |
| 4,407,761 | 10/1983 | Blum et al. | 260/502.5 |
| 4,621,077 | 11/1986 | Rosini et al. | 514/108 |
| 4,705,651 | 11/1987 | Staibano | 260/502.5 |
| 4,992,007 | 5/1990 | Kieczykowski | 562/13 |

FOREIGN PATENT DOCUMENTS

| | | |
|---|---|---|
| 0088462 | 9/1983 | European Pat. Off. . |
| 201057 | 11/1986 | European Pat. Off. ................ 31/65 |
| 0341961 | 5/1989 | European Pat. Off. . |
| WO91/05791 | 5/1991 | PCT Int'l Appl. . |

OTHER PUBLICATIONS

J. Am. Chem. Soc. 78: 4450–4452 (1956).
Synthesis (2): 135–137 (1990).
Derwent Abstract 90-161 353/21 of Fujisawa's JO 2104-593A.
Adzamli, et al., *Development of Phosphonate Derivatives of Gadolinium Chelates for NMR Imaging of Calcified Soft Tissues*, J. Med. Chem., vol. 32, pp. 139–144 (1989).

*Primary Examiner*—Howard T. Mars
*Assistant Examiner*—Kimberly J. Kestler
*Attorney, Agent, or Firm*—Robert J. North; Charles M. Caruso

[57] ABSTRACT

Described are new agents for treating bone disorders associated with a reduction in bone mass and abnormalities in bone resorption or bone formation including osteoporosis. Paget's disease, bone metastases and malignant hypercalcemia. The agents are hydroxyl containing steroidal hormones, having bone resorption antagonist or bone formation stimulatory activity, covalently linked through the hydroxyl group via a bond hydrolyzable in the human body, e.g. carbamate or carbonate, which is further covalently linked to an amino, or hydroxy substituted alkylidene-1,1-bisphosphonate, through the respective amino or hydroxy group. The alkyl bisphosphonate moiety confers bone affinity. The agent acts by delivering the steroidal hormone directly to the bone target site where it is released for bone resorption antagonist or bone formation stimulatory action by hydrolysis of the hydrolyzable covalent bond.

15 Claims, No Drawings

NOVEL BONE ACTING AGENTS

This is a continuation of application Ser. No. 07/644,178, filed on Jan. 22, 1991, now abandoned.

BACKGROUND OF THE INVENTION

1. Field of the Invention

The present invention relates to novel substituted amino or hydroxy alkyl-1,1-bisphosphonic acid compounds, processes for their preparation, pharmaceutical compositions containing them, and methods for their use as bone-affinity agents for delivering bone resorption or formation active drugs directly to the bone target site.

2. Brief Description of Disclosures in the Art

It is known that certain compounds exhibit an affinity for bone. In this context, an affinity for bone relates to the ability of the compound to bind to mineralized bone matrix with a tendency to accumulate in bone and to bind into the crystalline apatite structure. Tetracyclines, polymalonates and diphosphonates are representative compounds known to have an affinity for bone.

See, for example, U.S. Pat. No. 4,705,651 (assigned to Gentili) and U.S. Pat. No. 4,922,007 (assigned to Merck & Co. Inc.) which disclose the bone affinity agent, 4-amino-1-hydroxybutylidene-1,1-bisphosphonic acid and processes for its production.

It has previously been proposed to join a bone-seeking agent, such as tetracyline, to a carbonic anhydrase inhibitor through a bridging agent to provide compounds for the treatment or prophylaxis of degenerative bone diseases. See EP 201,057 (published Nov. 12, 1986).

Further, it is taught in Fujisawa's JO 2104-593A to link a hormone, e.g., calcitonin or insulin-like growth factor to an amino methylene bisphosphonic acid.

However, it is not taught or suggested in either reference that a hydroxyl containing steroidal hormone, such as 17-beta estradiol, norethandrolone, androsterone, norethindrone, or nandrolone, can be linked to an amino or hydroxy alkylidene bisphosphonic acid to produce an agent effective in treating bone disorders.

SUMMARY OF THE INVENTION

The present invention is based on discoveries related to the greater relative bone affinities of 1,1-bisphosphonates versus polymalonates described in the art. We have found that compounds having a hydroxyl containing steroidal hormone, which are linked through the hydroxyl to an amino or hydroxyl alkyl-1,1-bisphosphonic acid, through the respective amino or hydroxyl group, via a carbamate or carbonate type linkage, have an affinity for bone, where hydrolysis of the linkage occurs to liberate the steroidal hormone which can then exhibit a localized therapeutic effect on bone.

By this invention there is provided compounds of the formula:

A-B-C wherein:
A is a residue of a hydroxyl containing steroidal hormone possessing human bone resorption antagonist activity or bone formation stimulatory activity;
C is a residue of an amino or hydroxy alkyl-1,1-bisphosphonate, possessing human bone affinity; and
B is a covalent linkage, connecting A through the hydroxyl moiety and C through the respective amino or hydroxyl moiety, which linkage can hydrolyze in the human body in the vicinity of bone to release steroidal hormone A, and pharmaceutically acceptable salts or esters thereof.

Further provided is a compound of the formula:

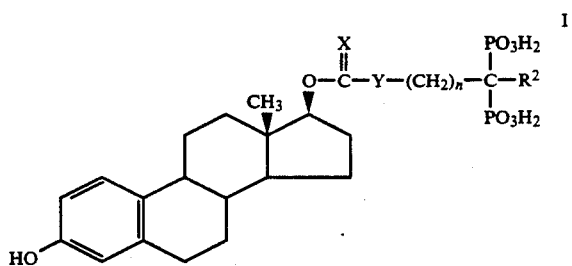

where
X is O, S;
Y is NH, O, $NR^1$, wherein $R^1$ is H or $C_1$-$C_4$ alkyl;
n is 1-4;
$R^2$ is H, OH,
and pharmaceutically acceptable salts or thereof.

Also provided is a compound of the formula:

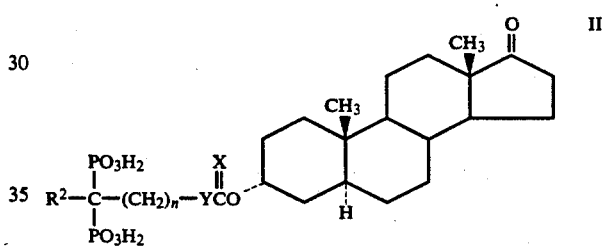

where
X is O, S;
Y is NH, O, $NR^1$, wherein $R^1$ is H or $C_1$-$C_4$-alkyl;
n is 1-4;
$R^2$ is H, OH;
and pharmaceutically acceptable salts thereof.

Furthermore, there is provided a compound of the formula:

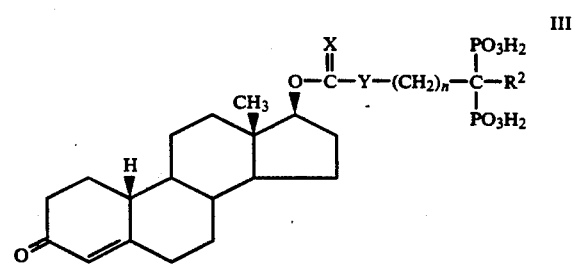

where
X is O, S;
Y is NH, O, $NR^1$, wherein $R^1$ is H or $C_1$-$C_4$-alkyl;
n is 1-4;
$R^2$ is H, OH;
and pharmaceutically acceptable salts thereof.

Additionally there is provided a compound being of the formula:

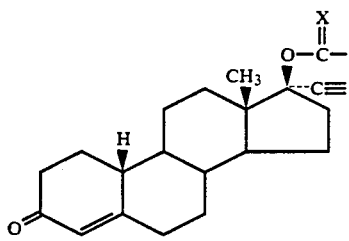

where
X is O, S;
Y is NH, O, $NR^1$, wherein $R^1$ is H or $C_1$-$C_4$-alkyl;
n is 1-4;
$R^2$ is H, OH;
and pharmaceutically acceptable salts thereof.

Also being provided are intermediates useful for producing the compounds of formula I, of the following formulas;

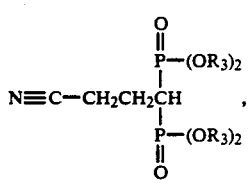

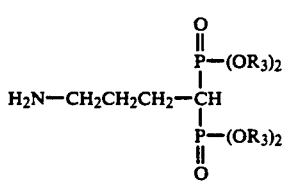

wherein $R_3$ is linear/branched $C_1$-$C_4$ alkyl.

Also provided is a pharmaceutical composition which comprises a compound described above and a pharmaceutically acceptable carrier.

Further provided is a method for treating bone diseases in a human host which comprises administering to said host a therapeutically effective amount of a compound described above.

BRIEF DESCRIPTION OF THE INVENTION AND PREFERRED EMBODIMENTS

The scope of the compounds of the present invention is defined above by the formula A—B—C and includes those characterized by the following structural formulae:

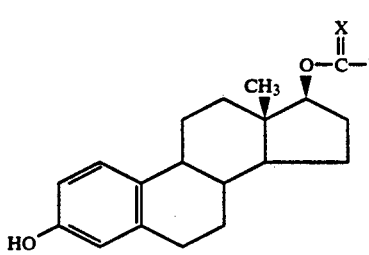

where
X is O, S;
Y is NH, O, $NR^1$, wherein $R^1$ is H or $C_1$-$C_4$ alkyl;
n is 1-4;
$R^2$ is H, OH;
and pharmaceutically acceptable salts or esters thereof.

In the main embodiment of the invention, the bone-affinity properties of the alkyl-1,1-bisphosphonic acid portion of the compound of formulas I-IV can be advantageously used as a drug delivery agent. Application of 1,1-bisphosphonic acids as drug delivery agents results in use of reduced amounts of the bone resorption or formation active drugs, thus lowering toxicity and other unwanted side effects related to these drugs.

The steroid drugs or agents which modulate bone resorption or stimulate bone formation in this invention may be drugs which act as either bone resorption inhibiting or bone formation stimulating agents such as bone active steroids. Representative examples of hydroxy-containing steroidal hormones known in the art inclose those listed in the MERCK INDEX, Eleventh Edition (1989) as follows (the therapeutic category and respective compound number are given for each):

ANABOLIC

Androisoxazole, 667
Androstenediol, 670
Bolandiol, 1325
Bolasterone, 1326
Clostebol, 2409
Ethylestrenol, 3761
Formyldienolone, 4161
4-Hydroxy-19-nortestosterone, 4768
Methandriol, 5861

Methenolone, 5887
Methyltrienolone, 6049
Nandrolone, 6280
Norbolethone, 6603
Oxymesterone, 6918
Stenbolone, 8763
Trenbolone, 9499

ANDROGEN

Boldenone, 1327
Fluoxymesterone, 4113
Mestanolone, 5816
Mesterolone, 5817
Methandrostenolone, 5862
17-Methyltestosterone, 6044
17α-Methyltestosterone 3-Cyclopentyl Enol Ether, 6045
Norethandrolone, 6613
Normethandrolone, 6629
Oxandrolone, 6875
Oxymesterone, 6918
Oxymetholone, 6920
Prasterone, 7710
Stanolone, 8753
Stanozolol, 8754
Testosterone, 9109
Tiomesterone, 9385

ESTROGEN

Equilenin, 3581
Equilin, 3582
Estradiol, 3653
Estradiol Benzoate, 3655
Estriol, 3659
Ethinyl Estradiol, 3689
Mestranol, 5819
Moxestrol, 6203
Mytatrienediol, 6254
Quinestradiol, 8065
Quinestrol, 8066

GLUCOCORTICOID

21-Acetoxypregnenolone, 70
Alclometasone, 213
Algestone, 229
Amcinonide, 398
Beclomethasone, 1029
Betamethasone, 1202
Budesonide, 1455
Chloroprednisone, 2157
Clobetasol, 2361
Clocortolone, 2368
Cloprednol, 2396
Corticosterone, 2532
Cortisone, 2533
Cortivazol, 2536
Deflazacort, 2852
Desonide, 2908
Desoximetasone, 2910
Dexamethasone, 2922
Diflorasone, 3126
Diflucortolone, 3129
Difluprednate, 3134
Enoxolone, 3543
Fluazacort, 4048
Flucloronide, 4053
Flumethasone, 4066
Flunisolide, 4071
Fluocinolone Acetonide, 4076
Fluocinonide, 4077
Fluocortin Butyl, 4078
Fluocortolone, 4079
Fluorometholone, 4104
Fluperolone Acetate, 4115
Fluprednidene Acetate, 4118
Fluprednisolone, 4119
Flurandrenolide, 4122
Formocortal, 4156
Halcinonide, 4504
Halometasone, 4510
Halopredone Acetate, 4512
Hydrocortamate, 4709
Hydrocortisone, 4710
Hydrocortisone Acetate, 4711
Hydrocortisone Phosphate, 4712
Hydrocortisone 21-Sodium Succinate, 4713
Hydrocortisone Tebutate, 4714
Mazipredone, 5644
Medrysone, 5679
Meprednisone, 5750
Methylprednisolone, 6028
Mometasone Furoate, 6151
Paramethasone, 6977
Prednicarbate, 7717
Prednisolone, 7719
Prednisolone 21-Diethylaminoacetate, 7720
Prednisolone Sodium Phosphate, 7721
Prednisolone Sodium Succinate, 7722
Prednisolone Sodium 21-m-Sulfobenzoate, 7723
Prednisolone 21-Stearoylglycolate, 7724
Prednisolone Tebutate, 7725
Prednisolone 21-Trimethylacetate, 7726
Prednisone, 7727
Prednival, 7728
Prednylidene, 7729
Prednylidene 21-Diethylaminoacetate, 7730
Tixocortol, 9408
Triamcinolone, 9511
Triamcinolone Acetonide, 9512
Triamcinolone Benetonide, 9513
Triamcinolone Hexacetonide, 9514

PROGESTOGEN

Allylestrenol, 289
Anagestone, 658
Desogestrel, 2906
Dimethisterone, 3208
Ethisterone, 3696
Ethynodiol, 3816
Flurogestone Acetate, 4125
Gestodene, 4308
17-Hydroxy-16-methylene-$\Delta^6$-progesterone, 4763
17α-Hydroxyprogesterone, 4773
Lynestrenol, 5501
Medroxyprogesterone, 5677
Melengestrol, 5697
Norethindrone, 6614
Norethynodrel, 6615
Norgesterone, 6619
Norgestrel, 6621
Norgestrienone, 6622
Norvinisterone, 6637
Pentagestrone, 7068

Preferred examples, are estrogens and synthetic steroidal compounds with estrogenic activity, such as 17- beta-estradiol, progestins such as norethindrone, androgens such as androsterone or norethandrolone, or anabolic agents such as nandrolone.

The alkyl-1,1-bisphosphonic acid moiety operable in this invention is of the formula:

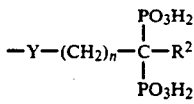

where Y is NH, O, $NR^1$, n is 1-4, preferably 3-4 and $R^2$ is H, OH or protected hydroxy, with the hydroxyl protecting group being pharmaceutically acceptable, e.g. acetate, succinate, benzoate, pamoate and the like and $R^1$ is H or $C_1$-$C_4$ alkyl. Preferably $R^2$ is H or OH.

Preparation of the aminoalkyl bisphosphonates of Structure I where $R^2$ is H and X is O is given in the Examples herein. Basically, the chlorocarbonate of the hydroxy containing steroidal hormone is prepared and reacted with the aminoalkyl bisphosphonate as described herein.

Where $R^2$ is OH, analogous preparations are described in U.S. Pat. Nos. 4,621,077, 4,705,651, 4,922,007 and 4,407,761.

Where the function, Y, is an amine substituted by $R^1$ being $C_1$-$C_4$ linear or branched alkyl, e.g. ethyl, analogous processes for making are known in the art. Generally, the amine function can be monoalkylated by e.g., reductive alkylation, prior to reaction with the chlorocarbonate of the steroidal hormone.

Where the function Y is an ether oxygen, —O—, these compounds can be made by reacting a hydroxyalkylidene bisphosphoric acid with the chlorocarbonate of the steroidal hormone. Where $R^2$ is OH, this is protected, during the reaction and later removed by conventional means.

Preparation of analogous hydroxyalkylidenediphosphonates where $R^2$=H or OH are also described in JACS Vol. 78, pp. 4451-2 (1956), Synthesis (2), pp. 135-7 by D. W. Hutchinson et al., U.S. Pat. Nos. 3,957,858, 3,962,318, 3,944,599, and 3,664,975.

Representative examples include

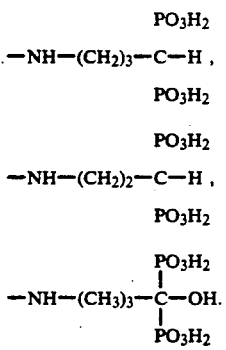

The covalent linking group where X is O or S, is formed by linking together the hydroxy containing steroidal hormone and the amine or hydroxy alkylidene bisphosphonate by the use of phosgene or thiophosgene respectively. If $R^2$ is hydroxy, or if the steroidal hormone contains another hydroxy besides the desired target hydroxy group, this can be protected by a conventional hydroxy protecting group, e.g. benzyl, prior to reaction with phosgene or thiophosgene and then later removed by conventional methods, e.g. catalytic hydrogenation with palladium on carbon.

The covalent linking group can be a carbamate,

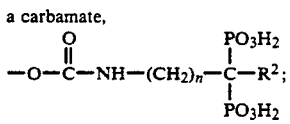

a thiocarbamate,

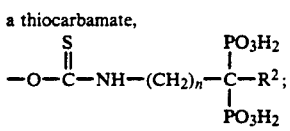

N-substituted carbamate

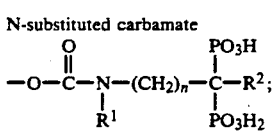

N-substituted thiocarbamate

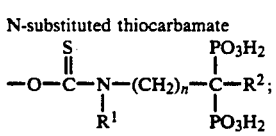

a carbonate,

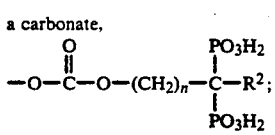

or thiocarbonate,

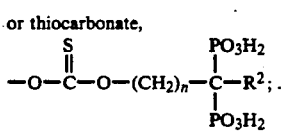

Methods of preparing the linking groups and the compounds of the instant invention will be readily seen by referral to the following Flow Chart.

As seen in the Flow Chart, 17-beta estradiol 1 is treated with benzyl halide in, e.g. anhydrous DMF, in the presence of NaH to produce the 3-benzylether protected 17-beta estradiol 2.

The benzylether 2 is then contacted with phosgene in, e.g., toluene to produce the chloroformate 3.

Intermediate VI, where $R_3$ can be $C_1$-$C_4$ linear/branched alkyl, and preferably methyl, is reacted with 3 to produce the tetraester. The tetraisopropyl ester 6 is illustrated here.

Tetraisopropyl methylene diphosphonate 4 is reacted with acrylonitrile in, e.g. dimethoxyethane in the presence of NaH under anhydrous conditions at room temperature, then at 80° C. for 5 hours, to produce the cyanopropyl-1,1-diphosphonate 5.

Compound 5 is catalytically reduced in, e.g. HOAc, under $H_2$ in the presence of $PtO_2$ catalyst to produce the 4-aminobutyl-1,1-diphosphonate 6.

The 4-aminobutyl 1,1-diphosphonate 6 is reacted with the chloroformate 3 in e.g., $CH_2Cl_2$, in the presence of a proton acceptor, e.g. pyridine, at room temperature to produce the carbamate 7.

The 3-benzyl blocking group in 7 is removed by catalytic hydrogenation in e.g., EtOH, under $H_2$ (e.g. 50 psig) using a 5% Pd/C catalyst at room temperature to yield the estradiol derivative 8.

Compound 8 is then desterified with e.g., trimethylsilylbromide in e.g., CH₂Cl₂ at e.g., room temperature under N₂ for e.g., 24 hours to produce the free acid 9.

The free diacid 9 can be converted to the preferred pharmaceutical dosage form, the disodium salt, by reaction with e.g., NaHCO₃ in water and then isolated by crystallization.

In similar manner, the 3-hydroxy group of androsterone, and the 17-hydroxy groups of norethindrone and nandrolone, can be converted to the corresponding chloroformate as 3, then reacted with the aminoalkylidene bisphosphonate 6, to form the corresponding ester of 7, and then hydrolyzed to form the corresponding bisphosphonic acid of 9, being respectively, II, III and IV.

The other hydroxy-containing steroids listed above from the Merck Index can be treated in like manner.

It will be obvious to one skilled in the art to make modifications in the choice of starting materials and process conditions to make all of the invention compounds disclosed herein.

FLOW CHART

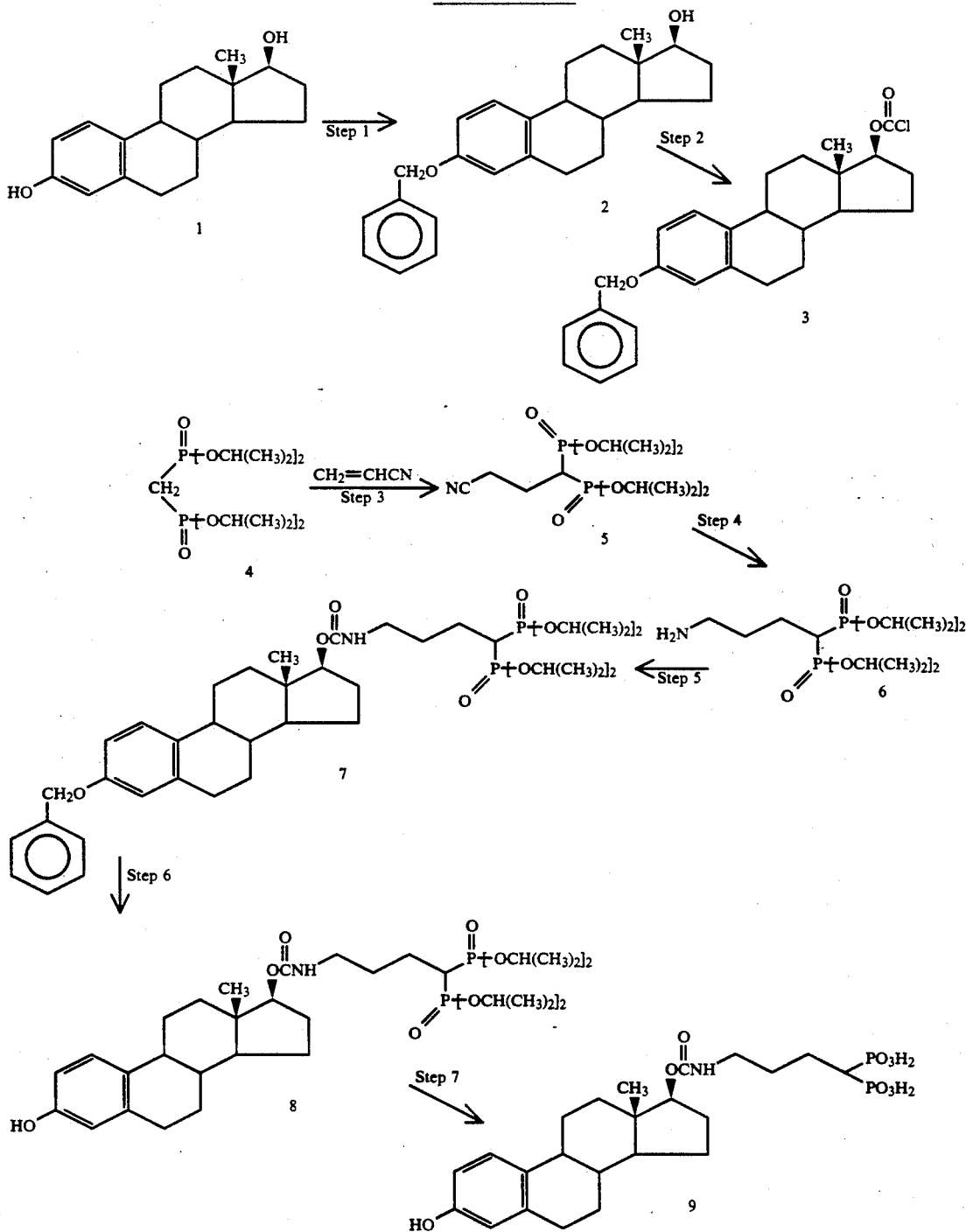

Included within the scope of this invention are all the enantiomers of any compound of the invention which exhibits optical isomerism. Additionally, all pharmaceutically acceptable salts of the compounds described herein, such as sodium, potassium, lithium, ammonium and the like, salts are also within the scope of this invention, which have a beneficial effect on bone resorption. "Halogen" as utilized herein means chlorine, fluorine, bromine and iodine.

Synthesis of the compounds of formulae I-IV are generally carried out by the following route. It will be readily apparent to one of ordinary skill in the art reviewing the synthetic routes depicted below that other compounds within formula I can be synthesized by substitution of appropriate reactants and agents in the synthesis shown below.

The magnitude of a prophylactic or therapeutic dose of the invention compound will vary with the nature or the severity of the condition to be treated and with the particular compound and its route of administration. In general, the daily dose range for bone resorption disease use lies within the range of from about 0.01 mg to about 10 mg per kg body weight of a mammal.

Any suitable route of administration may be employed for providing a mammal, especially a human, with an effective dosage of the compound. For example, oral, rectal, topical, parenteral, ocular, nasal, buccal, intravenous and the like may be employed. Dosage forms include tablets, troches, dispersions, suspensions, solutions, capsules, creams, ointments, aerosols and the like.

The pharmaceutical compositions of the present invention comprise the invention compound as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids or bases including inorganic and organic acids and bases. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray from pressurized packs or a nebuliser, or a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of the invention compounds include transdermal devices, aerosols, creams, ointments, lotions, dusting powder, and the like.

In practical use, the invention compound can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the invention compound may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing suitable machine, a mixture of the powdered compound moistened with an inert liquid diluent.

The following are examples of representative pharmaceutical dosage forms for the invention compound:

| Injectable Suspension (I.M.) | mg/ml |
| --- | --- |
| Compound of Example I | 2.0 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Example I | 25.0 |
| Microcrystalline Cellulose | 415.0 |
| Providone | 14.0 |
| Pregelatinized Starch | 43.5 |
| Magnesium Stearate | 2.5 |
| | 500 |

| Capsule | mg/capsule |
| --- | --- |
| Compound of Example I | 25.0 |
| Lactose Powder | 573.5 |
| Magnesium Stearate | 1.5 |
| | 600 |

The following examples are illustrative of the instant invention and should not be construed to be limits on the scope or spirit of the instant invention.

EXAMPLE 1

Synthesis of:
3-Hydroxy-17β-(4,4-diphosphonobutylaminocarbonyloxy)estra-1,3,5(10)-triene

Step A

3-Benzyloxy-17β-hydroxyestra-1,3,5(10)-triene

A solution of 3,17β-dihydroxyestra-1,3,5(10)-triene (4.73 g, 17.4 mmol) in DMF (10 mL) was added slowly to a stirred and cooled mixture of 60% NaH (1.1 g, 27.5 mmol) in DMF (10 mL). After addition was complete, the cooling bath was removed and the mixture stirred at room temperature for 1 hour until all of the NaH had reacted. Benzyl bromide (2.9 mL, 27.8 mmol) was added in a stream and the solution stirred at room temperature for 20 hours. After concentrating under reduced pressure, the residue was partitioned between EtOAc and 10% citric acid. The aqueous layer was extracted with EtOAc again and the organic extracts combined, washed with saturated $NaHCO_3$ solution, dried ($Na_2SO_4$), filtered and concentrated. The residue was triturated with $Et_2O$-hexane to give 5.38 g (85%) of the above-titled product, mp=97°–100°.

Step B

3-Benzyloxy-17β-chloracarbonyloxyestra-1,3,5(10)-triene

3-Benzyloxy-17β-hydroxyestra-1,3,5(10)-triene (1.0 g, 2.76 mmol) was added to 40 mL of a 12.5% solution of phosgene in toluene and the solution stirred at room temperature for 20 hours. Concentration under reduced pressure gave 1.1 g of the above-titled chloroformate.

Step C

Tetraisopropyl 3-cyanobutyl-1,1-diphosphonate

Tetraisopropyl methylenediphosphonate (18.3 g, 50.3 mmol) was added over 20 minutes to a stirred suspension of 60% NaH (2.44 g, 61 mmol) in dimethoxyethane (100 mL) under $N_2$ and the mixture was stirred at room temperature for 20 minutes. After adding 4.0 ml. 61 mM, acrylonitrile, the solution was heated at 80° for 5 hours and then stirred at room temperature for 20 hours. Glacial HOAc (4.0 mL, 70 mmol) was added, the mixture stirred at room temperature for 30 minutes and then concentrated under reduced pressure. Several $Et_2O$ extracts of the gummy residue were combined and concentrated. Flash chromatography over silica gel and elution with 1% MeOH/99% $CHCl_3$ gave 5.15 g (26%) of pure above-titled product.

Step D

Tetraisopropyl 4-aminobutyl-1,1-diphosphonate

A solution of tetraisopropyl 3-cyanopropyl-1,1-diphosphonate (5.15 g, 13 mmol) in HOAc (100 mL) containing concentrated HCl (2.15 mL) and $PtO_2$ catalyst (0.40 g) was hydrogenated in a Parr apparatus at an initial pressure of 50 psig for 20 hours. After filtering through diatomaceous earth and concentrating, the residue was partitioned between saturated $NaHCO_3$ solution and $CH_2Cl_2$. The organic extracts were dried ($Na_2SO_4$), filtered and concentrated to give 3.72 g (71%) of the above-titled amine.

Step E

3-Benzyloxy-17β-(4,4-diphosphonobutylaminocarbonyloxy)-estra-1,3,5(10)-triene tetraisopropyl ester Pyridine (0.32 mL, 3.9 mmol) was added to a solution of 3-benzyloxy-17β-chlorcarbonyloxyestra-1,3,5(10)-triene (1.1 g, 2.6 mmol) and tetraisopropyl 4-aminobutyl-1,1-diphosphonate (1.57 g, 3.9 mmol) in $CH_2Cl_2$ (20 mL) and the mixture stirred at room temperature for 3 days. After concentrating under reduced pressure, the residue was flash chromatographed over silica gel and 1.68 g (82%) of the above-titled product eluted with 2% MeOH-98% $CHCl_3$.

Step F 3-hydroxy-17 beta-(4,4-diphosphonobutylaminocarbonyloxy)-estra-1,3,5(10)-triene tetraisopropyl ester A solution of the benzyl ether of Step E (0.53 g, 0.67 mmol) in EtOH (50 mL) was hydrogenated in a Parr apparatus at 50 psig in the presence of a 5% Pd on C catalyst (210 mg) for 2 hours. After filtering through diatomaceous earth and concentrating, the residue was flash chromatographed over silica gel and 0.42 g (89%) of the above-titled product eluted with 3.5% MeOH-96.5% $CHCl_3$.

Step G

3-Hydroxy-17β-(4,4-diphosphonobutylaminocarbonyloxy)-estra-1,3,5(10)-triene

Trimethylsilylbromide (0.40 mL, 3.03 mmol) was added to a solution of the tetraisopropyl ester of Step F (0.42 g, 0.60 mmol) in $CH_2Cl_2$ (6.0 mL) and the mixture stirred at room temperature under $N_2$ for 24 hours. The solution was concentrated under reduced pressure and the residue taken up in distilled $H_2O$ (20 mL). After filtering, the filtrate was lyophilized to give 330 mg (97%) of the above-titled diphosphonic acid as the dihydrate.

Anal. for $C_{23}H_{35}NO_9P_2.2H_2O$: Calcd. C, 48.68; H, 6.93; N, 2.47. Found: C, 48.85; H, 6.90; N, 2.05.

The disodium salt was prepared by neutralizing the diphosphonic acid (130 mg, 0.23 mmol) with $NaHCO_3$ (40.3 mg, 0.48 mmol) in $H_2O$ (5 mL) for 1 hour at room temperature then concentrating to 3 mL under reduced pressure. EtOH (3 mL) was added and the mixture cooled. After centrifugation, solvent was pipetted off and the residue solid triturated three times with absolute EtOH. Drying under high vacuum afforded the disodium salt (52 mg). An additional 60 mg of sodium salt could be recovered from the filtrate by concentration and trituration with absolute EtOH.

Anal. for $C_{23}H_{33}NNa_2O_9P_2.H_2O$: Calcd. C, 46.54; H, 5.94; N, 2.36. Found: C, 46.42; H, 6.09; N, 2.13.

EXAMPLE 2

Synthesis of:
3α-(4,4-Diphosphonobutylaminocarbonyloxy)-5α-androstan-17-one

Step A

3α-(4,4-diphosphonobutylaminocarbonyloxy)-5α-androstan-17-one, Tetraisopropyl ester A solution of 3α-(chlorocarbonyloxy)-5α-androstan-17-one (353 mg, 1.0 mmol), tetraisopropyl 4-aminobutyl-1,1-diphosphonate (401 mg, 1.0 mmol) and pyridine (79 mg, 1 mmol) in $CH_2Cl_2$ (25 mL) is stirred at room temperature for 3 days. After concentrating under reduced pressure, the residue is flash chromatographed over silica gel and the carbamate product eluted with a MeOH—$CHCl_3$ solvent mixture.

Step B

3α-(4,4-diphosphonobutylaminocarbonyloxy)-5α-androstan-17-one

Trimethylsilyl bromide (0.33 mL, 2.5 mmol) is added to a solution of the tetraisopropyl ester of Step A (358 mg, 0.50 mmol) in $CH_2Cl_2$ (15 mL) and the mixture stirred at room temperature under $N_2$ for 2 days. After concentrating under reduced pressure the residue is taken up in distilled water, filtered and freeze-dried to give the titled diphosphonic acid product.

EXAMPLE 3

Synthesis of:
17β-(4,4-Diphosphonobutylaminocarbonyloxy)-4-estren-3-one

Step A

17β-(4,4-Diphosphonobutylaminocarbonyloxy)-4-estren-3-one, Tetraisopropyl Ester

A solution of 17β-(chlorocarbonyloxy)-4-estren-3-one (337 mg, 1.0 mmol), tetraisopropyl 4-aminobutyl-1,1-diphosphonate (401 mg, 1.0 mmol) and pyridine (79 mg, 1 mmol) in $CH_2Cl_2$ (20 mL) is stirred at room temperature for 3 days. After concentrating under reduced pressure, the residue is flash chromatographed over silica gel and the carbamate product eluted with a MeOH—$CHCl_3$ solvent mixture.

Step B

17β-(4,4-Diphosphonobutylaminocarbonyloxy)-4-estren-3-one

A mixture of the tetraisopropyl ester of Step A (246 mg, 0.35 mmol) and bromotrimethylsilane (0.23 mL, 1.75 mmol) in $CH_2Cl_2$ (15 mL) is stirred under $N_2$ at room temperature for 3 days. After concentrating under reduced pressure, the residue is triturated with distilled water, filtered and lyophilized to give the titled diphosphonic acid product.

EXAMPLE 4

Synthesis of:
17α-Ethynyl-17β-(4,4-diphosphonobutylaminocarbonyloxy)-19-nor-4-androsten-3-one

Step A

17α-Ethynyl-17β-(4,4-diphosphonobutylaminocarbonyloxy)-19-nor-4-androsten-3-one, Tetraisopropyl Ester.

A solution of norethindrone-17β-chloroformate (361 mg, 1 mmol), tetraisopropyl (4-aminobutyl-1,1-diphosphonate (401 mg, 1 mmol) and triethylamine (0.14 mL, 1 mmol) in $CH_2Cl_2$ (25 mL) is stirred at room temperature for 2 days. After concentrating under reduced pressure, the residue is flash chromatographed over silica gel and the carbamate product eluted with a MeOH—$CHCl_3$ solvent mixture.

Step B

17α-Ethynyl-17β-(4,4-diphosphonobutylaminocarbonyloxy)-19-nor-4-androsten-3-one

A mixture of the tetraisopropyl ester of Step A (290 mg, 0.40 mmol) and bromotrimethylsilane (0.26 mL, 2.0 mmol) in $CH_2Cl_2$ (15 mL) is stirred under $N_2$ at room temperature for 3 days. After concentrating under reduced pressure, the residue is triturated with distilled water, filtered and freeze-dried to give the titled disphosphonic acid product.

What is claimed is:

1. A compound of the formula:

A-B-C wherein:
A is a residue of a hydroxyl containing steroidal hormone possessing human bone resorption antagonist activity or bone formation stimulatory activity;
C is a residue of an amino or hydroxy alkyl-1,1-bisphosphonate, possessing human bone affinity; and
B is a covalent linkage selected from the group consisting of carbamate, carbonate, thiocarbamate, and thiocarbonate, connecting A through the hydroxyl moiety to C through the respective amino or hydroxyl moiety, which linkage can hydrolyze in the human body in the vicinity of bone to release steroidal hormone A, and pharmaceutically acceptable salts or esters thereof.

2. The compound of claim 1 wherein said steroidal hormone is selected from:
Androisoxazole,
Androstenediol,
Bolandiol,
Bolasterone,
Clostebol,
Ethylestrenol,
Formyldienolone,
4-Hydroxy-19-nortestosterone
Methandriol,
Methenolone,
Methyltrienolone,
Nandrolone,
Norbolethone,
Oxymesterone,
Stenbolone,
Trenbolone,
Boldenone,
Fluoxymesterone,
Mestanolone,
Mesterolone,
Methandrostenolone,
17-Methyltestosterone,
17α-Methyltestosterone 3-Cyclopentyl Enol Ether,
Norethandrolone,
Normethandrone,
Oxandrolone,
Oxymesterone,
Oxymetholone,
Prasterone,
Stanolone,
Stanozolol,
Testosterone,
Tiomesterone,
Equilenin,
Equilin, 17β-Estradiol,
Estradiol Benzoate,
Estriol,
Ethinyl Estradiol,
Mestranol,
Moxestrol,
Mytatrienediol,
Quinestradiol,
Quinestrol,
Glucocorticoid
21-Acetoxypregnenolone,
Alclometasone,
Algestone,
Amcinonide,
Beclomethasone,
Betamethasone,
Budesonide,
Chloroprednisone,
Clobetasol,
Clocortolone,
Cloprednol,
Corticosterone,
Cortisone,
Cortivazol,
Deflazacort,
Desonide,
Desoximetasone,
Dexamethasone,
Diflorasone,
Diflucortolone,
Difluprednate,
Enoxolone,
Fluazacort,
Flucloronide,
Flumethasone,
Flunisolide,
Fluocinolone Acetonide,
Fluocinonide,
Fluocortin Butyl,
Fluocortolone,
Fluorometholone,
Fluperolone Acetate,
Fluprednidene Acetate,
Fluprednisolone,
Flurandrenolide,
Formocortal,
Halcinonide,
Halometasone,
Halopredone Acetate,
Hydrocortamate,
Hydrocortisone,
Hydrocortisone Acetate,
Hydrocortisone Phosphate,
Hydrocortisone 21-Sodium Succinate,
Hydrocortisone Tebutate,
Mazipredone,
Medrysone,
Meprednisone,
Methylprednisolone,
Mometasone Furoate,
Paramethasone,
Prednicarbate,
Prenisolone,
Prednisolone 21-Diethylaminoacetate,
Prednisolone Sodium Phosphate,
Prednisolone Sodium Succinate,
Prednisolone Sodium 21-m-Sulfobenzoate,
Prednisolone 21-Stearoylglycolate,
Prednisolone Tebutate,
Prednisolone 21-Trimethylacetate,
Prednisone,
Prednival,
Prednylidene,
Prednylidene 21-Diethylaminoacetate,
Tixocortol,
Triamcinolone,
Triamcinolone Acetonide,
Triamcinolone Benetonide,
Triamcinolone Hexacetonide,
Allylestrenol,
Anagestone,
Desogestrel,
Dimethisterone,
Ethisterone,
Ethynodiol,
Flurogestone Acetate,
Gestodene,
17-Hydroxy-16-methylene-$\Delta^6$-progesterone,
17α-Hydroxyprogesterone,
Lynestrenol,
Medroxyprogesterone,
Melengestrol,
Norethindrone,
Norethynodrel,
Norgesterone,
Norgestrel,
Norgestrienone,
Norvinisterone,
Pentagestrone.

3. The compound of claim 2 wherein said steroidal hormone is selected from 17-beta estradiol, norethandrolone, androsterone, norethindrone, and nandrolone.

4. The compound of claim 1 wherein B is a carbamate linkage.

5. The compound of claim 1 wherein C is of the formula:

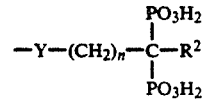

where
Y is NH, O, NR$^1$, wherein R$^1$ is H or C$_1$–C$_4$ alkyl;
n is 1–4; and
R$^2$ is H, OH.

6. The compound of claim 1 of the formula:

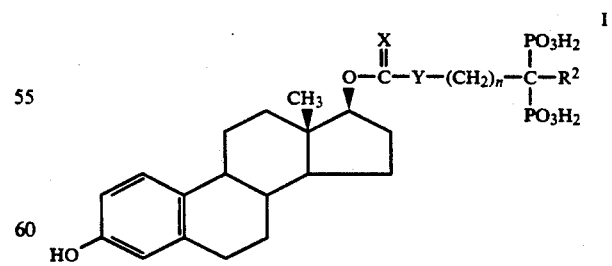

where
X is O, S;
Y is NH, O, NR$^1$, wherein R$^1$ is H or C$_1$–C$_4$ alkyl;
n is 1–4;
R$^2$ is H, OH,
and pharmaceutically acceptable salts or thereof.

7. The compound of claim 6 being of the formula:

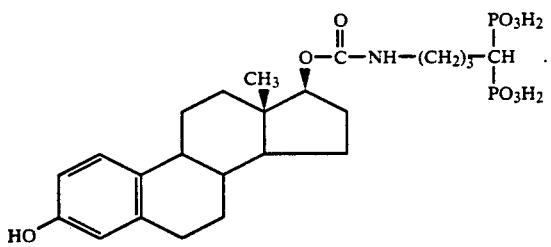

8. The compound of claim 1 of the formula:

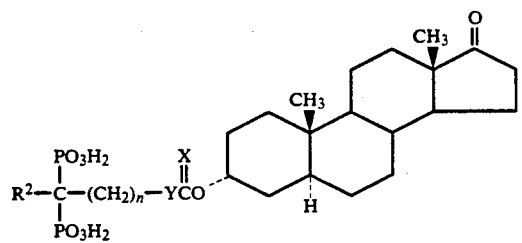

where
X is O, S;
Y is NH, O, NR$^1$, wherein R$^1$ is H or C$_1$-C$_4$ alkyl;
n is 1–4;
R$^2$ is H, OH;
and pharmaceutically acceptable salts thereof.

9. The compound of claim 8 being of the formula:

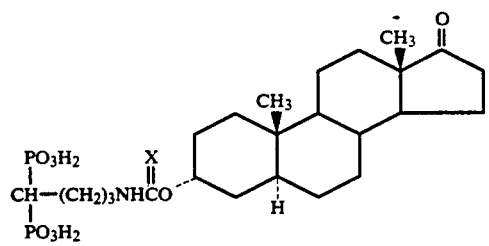

10. The compound of claim 1 of the formula:

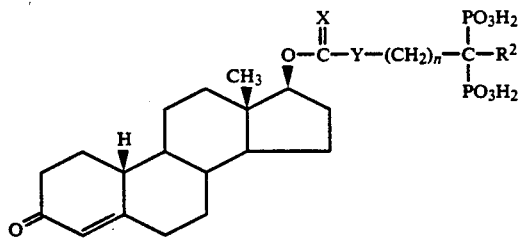

where
X is O, S;
Y is NH, O, NR$^1$, wherein R$^1$ is H or C$_1$-C$_4$ alkyl;
n is 1–4;
R$^2$ is H, OH;
and pharmaceutically acceptable salts thereof.

11. The compound of claim 10 being of the formula:

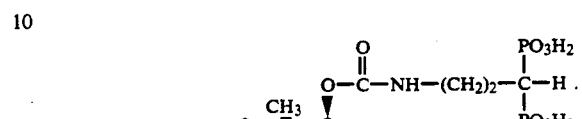

12. The compound of claim 1 being of the formula:

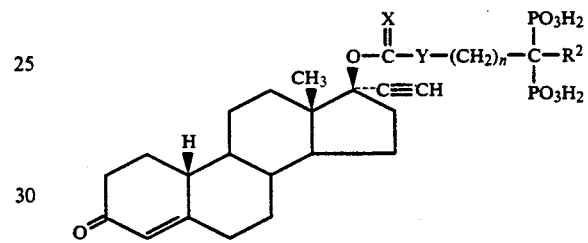

where
X is O, S;
Y is NH, O, NR$^1$, wherein R$^1$ is H or C$_1$-C$_4$ alkyl;
n is 1–4;
R$^2$ is H, OH;
and pharmaceutically acceptable salts thereof.

13. The compound of claim 12 being of the formula:

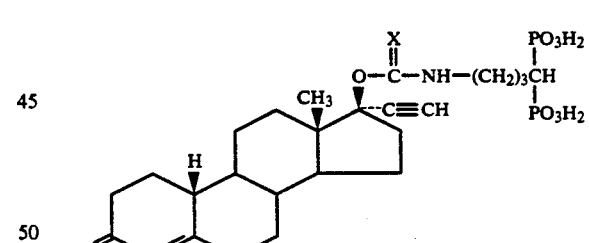

14. A pharmaceutical composition which comprises a compound according to claim 1 and a pharmaceutically acceptable carrier.

15. A method for treating bone diseases in a human host which comprises administering to said host a therapeutically effective amount of a compound of claim 1.

* * * * *